(12) United States Patent
Zang et al.

(10) Patent No.: US 8,138,823 B2
(45) Date of Patent: Mar. 20, 2012

(54) VOLTAGE GENERATING CIRCUIT AND ULTRASONIC DIAGNOSING DEVICE

(75) Inventors: Xinping Zang, Wuxi (CN); Shinichi Amemiya, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 159 days.

(21) Appl. No.: 12/509,203

(22) Filed: Jul. 24, 2009

(65) Prior Publication Data
US 2010/0019833 A1  Jan. 28, 2010

(30) Foreign Application Priority Data
Jul. 24, 2008 (CN) .......................... 2008 1 0134359

(51) Int. Cl.
*G05F 3/08* (2006.01)
*A61B 8/00* (2006.01)
(52) U.S. Cl. .................. 327/540; 331/186; 600/437
(58) Field of Classification Search ................. None
See application file for complete search history.

(56) References Cited

U.S. PATENT DOCUMENTS

| 3,727,216 | A  | * | 4/1973 | Antonio ........................ 342/28 |
| 5,444,412 | A  | * | 8/1995 | Kowalski ...................... 327/541 |
| 5,610,509 | A  |   | 3/1997 | Nustad |
| 6,328,697 | B1 |   | 12/2001 | Fraser |
| 6,570,435 | B1 | * | 5/2003 | Hastings ...................... 327/536 |
| 6,572,546 | B1 |   | 6/2003 | Bax et al. |
| 6,645,145 | B1 |   | 11/2003 | Dreschel et al. |
| 6,680,876 | B2 | * | 1/2004 | Isomichi et al. .............. 367/128 |
| 6,752,761 | B2 |   | 6/2004 | Amemiya |
| 6,795,374 | B2 |   | 9/2004 | Barnes et al. |
| 7,351,204 | B2 |   | 4/2008 | Amemiya |
| 7,394,306 | B2 | * | 7/2008 | Chen ............................ 327/541 |
| 2007/0106159 | A1 | * | 5/2007 | Iwama ........................ 600/459 |
| 2007/0228994 | A1 | * | 10/2007 | Hung et al. ................... 315/247 |

FOREIGN PATENT DOCUMENTS
JP  2004-236869  8/2004
* cited by examiner

Primary Examiner — Lincoln Donovan
Assistant Examiner — Terry L Englund
(74) Attorney, Agent, or Firm — Armstrong Teasdale LLP (57) ABSTRACT

A voltage generating circuit generates a voltage for driving an ultrasonic oscillator, and includes a multi-stage connected power supply circuit without a transformer.

18 Claims, 10 Drawing Sheets

FIG. 10

VOLTAGE GENERATING CIRCUIT AND ULTRASONIC DIAGNOSING DEVICE

FIELD OF THE INVENTION

The embodiments described herein relate to a voltage generating circuit for generating a voltage that drives an ultrasonic oscillator, and to an ultrasonic diagnosing device.

CROSS REFERENCE TO RELATED APPLICATIONS

This application claims the benefit of Chinese Patent Application No. 200810134359.2 filed Jul. 24, 2008, which is hereby incorporated by reference in its entirety.

BACKGROUND OF THE INVENTION

In an ultrasonic diagnosing device, a voltage is applied to an ultrasonic oscillator made of a piezoelectric material to oscillate the same and thereby transmit an ultrasonic wave. Accordingly, the ultrasonic diagnosing device has a voltage generating circuit for generating a voltage that drives the ultrasonic oscillator. For example, reference can be made to the gazette of Japanese Laid-Open Patent Publication No. 2004-236869.

In the case that, for example, a battery is used as a power supply of the voltage generating circuit, a voltage supplied by the battery is a comparatively low voltage (specifically below 15V). Therefore, the voltage generating circuit is required to generate a high output voltage (specifically 20V-50V) from the comparatively low voltage. An inverse converter has been used in the past as the voltage generating circuit that meets said requirement, and said inverse converter is a switch handover converter using a transformer.

However, since the inverse converter uses the transformer, it is very hard to raise a switching frequency above a specified frequency. The required capacity of circuit components that includes the capacitance of capacitors on a mounting substrate is inversely proportional to a square root of the switching frequency in nature. So the higher the switching frequency is, the less the required capacity is, thus reducing volume of the circuit components. However, it is very hard to raise the switching frequency above the specified frequency in said inverse converter, so the volume of the circuit components cannot be reduced and miniaturization of the mounting substrate is almost impossible. Moreover, due to a height of the transformer of the inverse converter, it is very hard to realize thinning of the mounting substrate. It can be seen above that when using the inverse converter, the miniaturization and thinning of the mounting substrate are restricted.

BRIEF DESCRIPTION OF THE INVENTION

Embodiments described herein provide a voltage generating circuit that generates a voltage for driving an ultrasonic oscillator and an ultrasonic diagnosing device having said voltage generating circuit. The voltage generating circuit and ultrasonic diagnosing device are the same as the conventional inverse converter in that they can generate a high output voltage from a relatively low input voltage. In addition, they can realize the above-mentioned miniaturization and thinning of the mounting substrate, which are difficult in the inverse converter.

In a first perspective, a voltage generating circuit is provided which can generate a voltage for driving an ultrasonic oscillator, characterized by a multi-stage connected power supply circuit without using a transformer.

In a second perspective, at least one stage of the multi-stage power supply circuit has an output voltage regulating part for regulating an output voltage into a desired voltage.

In a third perspective, the multi-stage power supply circuit is a two-stage power supply circuit.

In a fourth perspective, in the two-stage power supply circuit, the first stage of the power supply circuit is a constant voltage circuit whose output voltage is higher than the input voltage thereof, and the second stage of the power supply circuit has the output voltage regulating part.

In a fifth perspective, a maximum output voltage that can be obtained is 20 times an input voltage.

In a sixth perspective, an input voltage is below 15V and an absolute values of an output voltage is 10-70V.

In a seventh perspective, a battery is used as a power supply.

In an eighth perspective, the first stage of the power supply circuit is a boost converting circuit, and the second stage of the power supply circuit is a Single Ended Primary Inductance Converter (SEPIC) circuit.

In a ninth perspective, the first stage of and second stage of the power supply circuit are both SEPIC circuits.

In a tenth perspective, the SEPIC circuit used as the second stage generates a positive voltage and a negative voltage having equal absolute values as output voltages.

In an eleventh perspective, the first stage of the power supply circuit is an SEPIC circuit, and the second stage of the power supply circuit is a boost converting circuit.

In a twelfth perspective, the first stage of and second stage of the power supply circuit are both boost converting circuits.

In a thirteenth perspective, the second stage of the power supply circuit has a plurality of circuits.

In a fourteenth perspective, the plurality of circuits in the second stage of the power supply circuit are circuits that generate voltages of different absolute values.

In a fifteenth perspective, a voltage generated by the first stage of the power supply circuit is supplied not only to the second stage of the power supply circuit, but also to other loads than the ultrasonic oscillator in the ultrasonic diagnosing device.

In a sixteenth perspective, the voltage regulating part regulates the output voltage according to a type of a transmission mode of an ultrasonic wave.

In a seventeenth perspective, an ultrasonic diagnosing includes the voltage generating circuit of any of the first to sixteenth perspectives.

According to the first perspective, a multi-stage connected power supply circuit does not use a transformer. A power supply circuit that does not use a transformer cannot increase an input voltage to be as high as an output voltage of a power supply circuit that uses the transformer, but by a multi-stage connection, at least the output voltage of the power supply circuit that does not use the transformer can be equal to that of the power supply circuit that uses the transformer. Therefore, as with a conventional inverse converter, it can generate a high output voltage from a relatively low input voltage. Further, since the power supply circuit is the one that does not use the transformer, it can be much thinner than the conventional inverse converter. In addition, since no transformer is used, a switching frequency can be increased and volume of circuit components can be reduced, thus realizing miniaturization and thinning of a mounting substrate.

According to the second perspective, the desired output voltage can be obtained through the output voltage regulating part.

According to the third perspective, a high output voltage can be obtained from a relatively low input voltage through the two-stage power supply circuit.

According to the fourth perspective, the output voltage of the first stage of the power supply circuit becomes a high voltage that is higher than the input voltage, and the output voltage of the second stage of the power supply circuit reaches the desired voltage.

According to the fifth and sixth perspectives, from the low input voltage that is input to the first stage of the power supply circuit, a high output voltage used as the output voltage of said second stage of the power supply circuit can be obtained.

According to the seventh perspective, a voltage is supplied to the battery as an input voltage.

According to the eighth perspective, a high output voltage can be obtained from a relatively low input voltage through the boost converting circuit used as the first stage and the SEPIC circuit used as the second stage. In addition, the boost converting circuit and the SEPIC circuit are circuits that do not use transformers, so they can realize miniaturization of the mounting substrate.

According to the ninth perspective, a high output voltage can be obtained from the relatively low input voltage through the SEPIC circuit used as the first stage and the SEPIC circuit used as the second stage. In addition, the SEPIC circuits are circuits that do not use transformers, so they can realize miniaturization and thinning of the mounting substrate.

According to the tenth perspective, as voltages applied to the ultrasonic oscillator, a positive voltage and a negative voltage having equal absolute values can be obtained.

According to the eleventh perspective, a high output voltage can be obtained from the relatively low input voltage through the SEPIC circuit used as the first stage and the boost converting circuit used as the second stage. In addition, the SEPIC circuit and said the boost converting circuit are circuits that do not use transformers, so they can realize miniaturization and thinning of the mounting substrate.

According to the twelfth perspective, a high output voltage can be obtained from the relatively low input voltage through the boost converting circuit used as the first stage and the boost converting circuit used as the second stage. In addition, the boost converting circuits are circuits that do not use transformers, so they can realize miniaturization of the mounting substrate.

According to the thirteenth perspective, in the case that the second stage of the power supply circuit has a plurality of circuits, the plurality of circuits share the first stage of the power supply circuit, so the size of the mounting substrate can be controlled.

According to the fourteenth perspective, output voltages of different absolute values can be obtained in the plurality of circuits of the second stage of the power supply circuit.

According to the fifteenth perspective, the first stage of the power supply circuit can be used as a power supply circuit that generates the voltage to be supplied to other loads than the ultrasonic oscillator in the ultrasonic diagnosing device, so the size of the mounting substrate can be controlled.

According to the sixteenth perspective, different output voltages can be obtained as voltages for driving the ultrasonic oscillator according to the types of the transmission mode like B-mode or Doppler mode.

According to the seventeenth perspective, an ultrasonic diagnosing device can be obtained that has the same effect as any of the first to sixteenth perspectives.

DETAILED DESCRIPTION OF THE INVENTION

Figure 1:
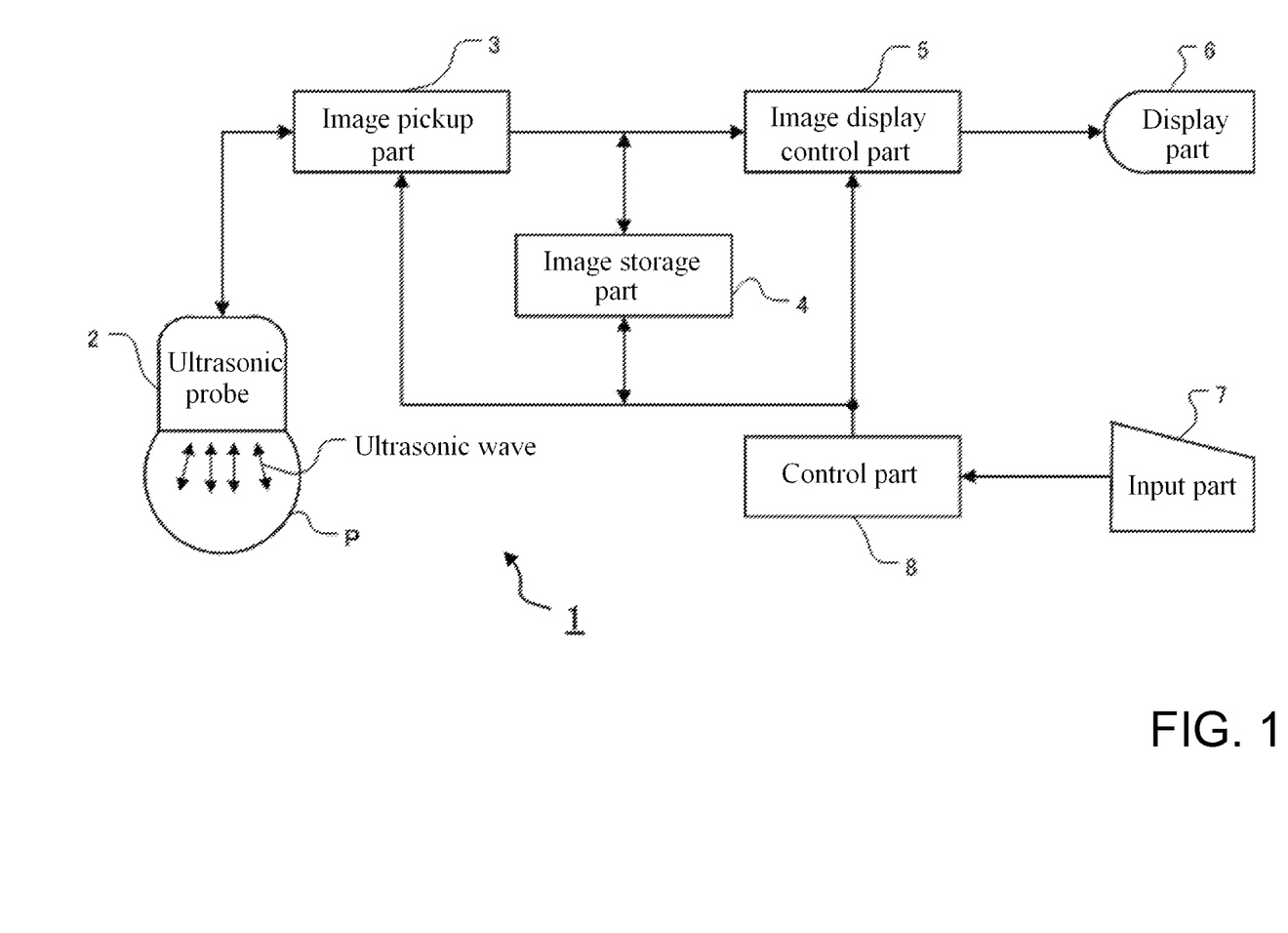
FIG. 1 is a block diagram showing an example of an overall structure of an ultrasonic diagnosing device having a voltage generating circuit according to the present invention.
Figure 2:
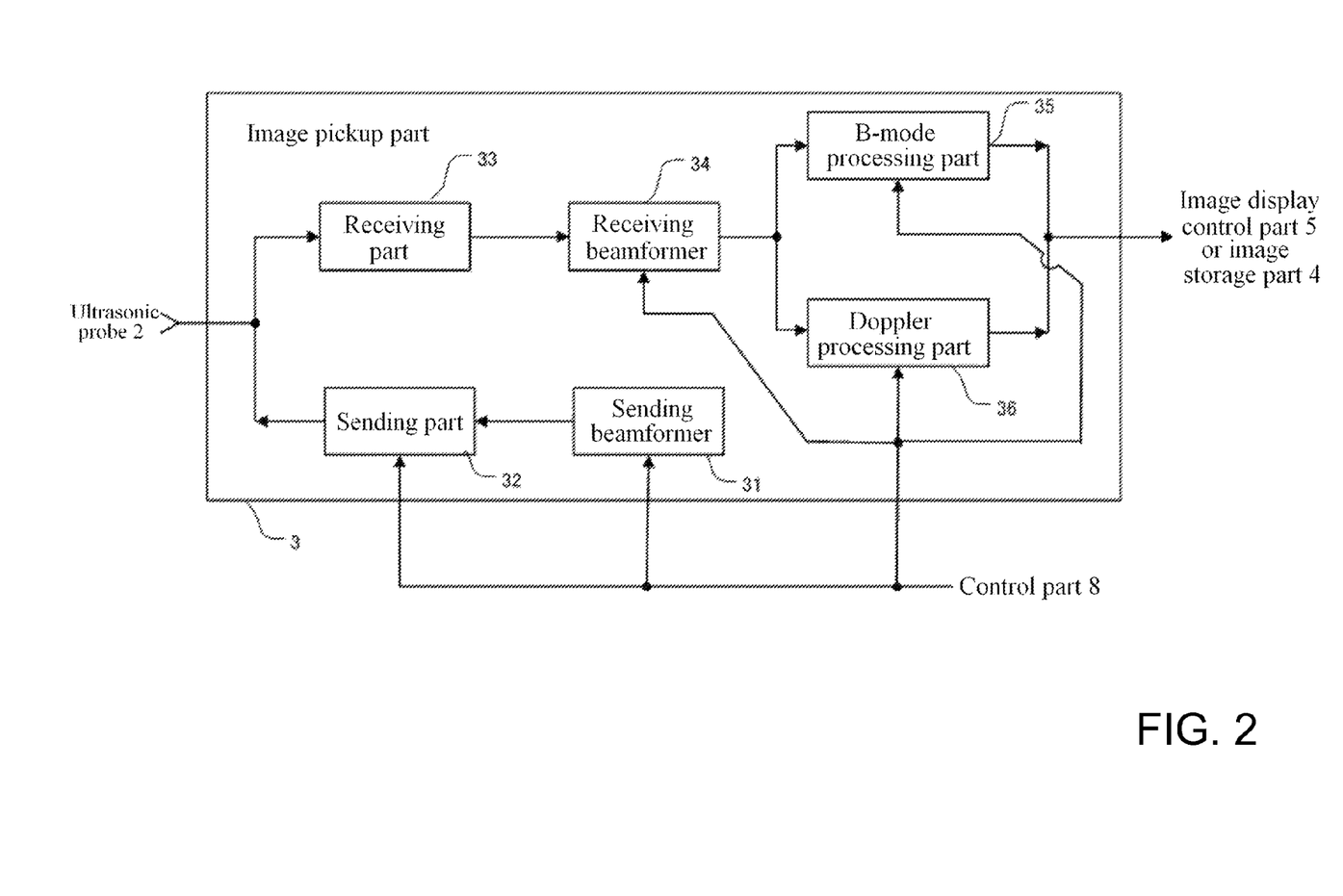
FIG. 2 is a block diagram showing a structure of an image acquiring part of the ultrasonic diagnosing device as shown in FIG. 1.
Figure 3:
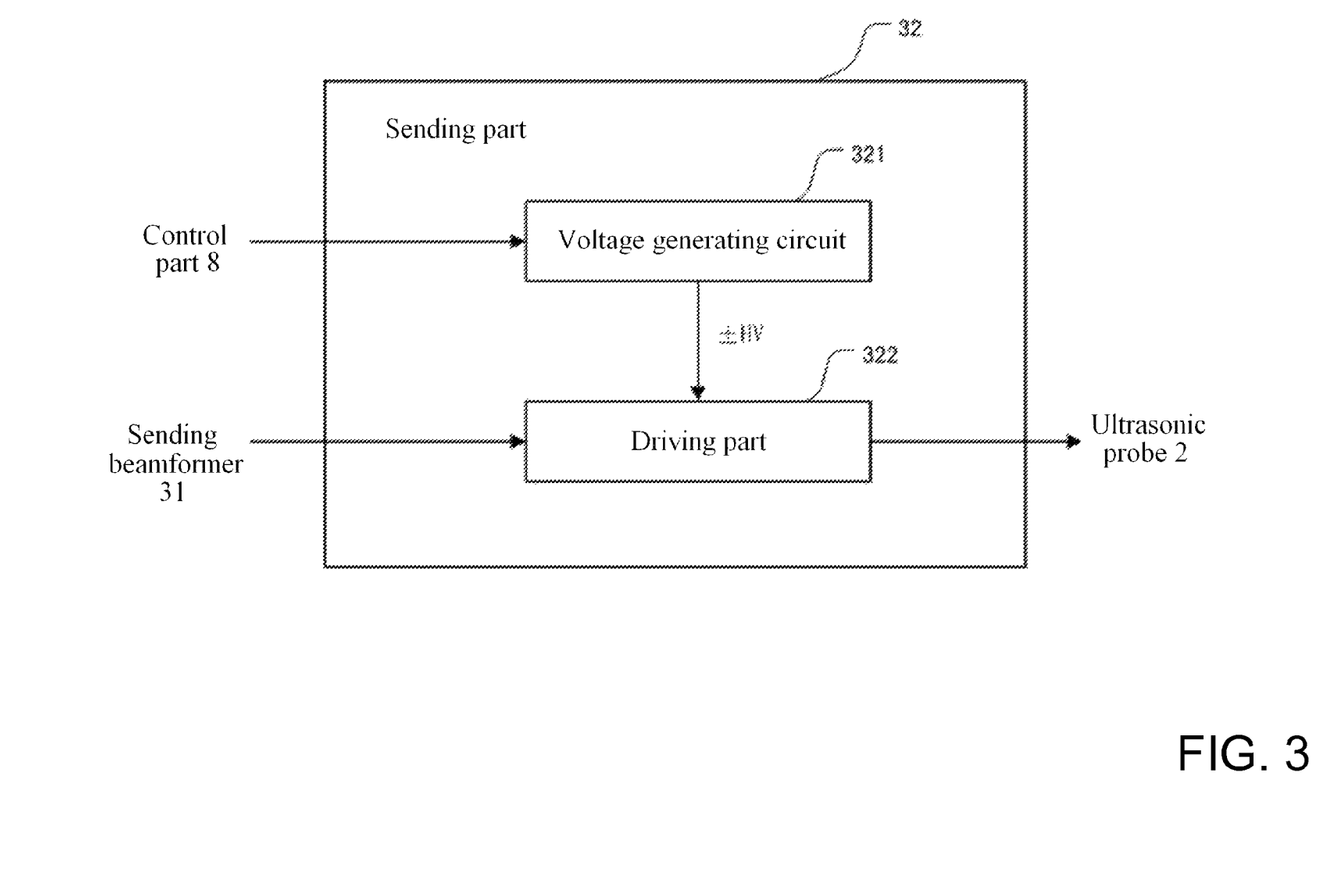
FIG. 3 is a block diagram showing a structure of a sending part in the image acquiring part as shown in FIG. 2.
Figure 4:
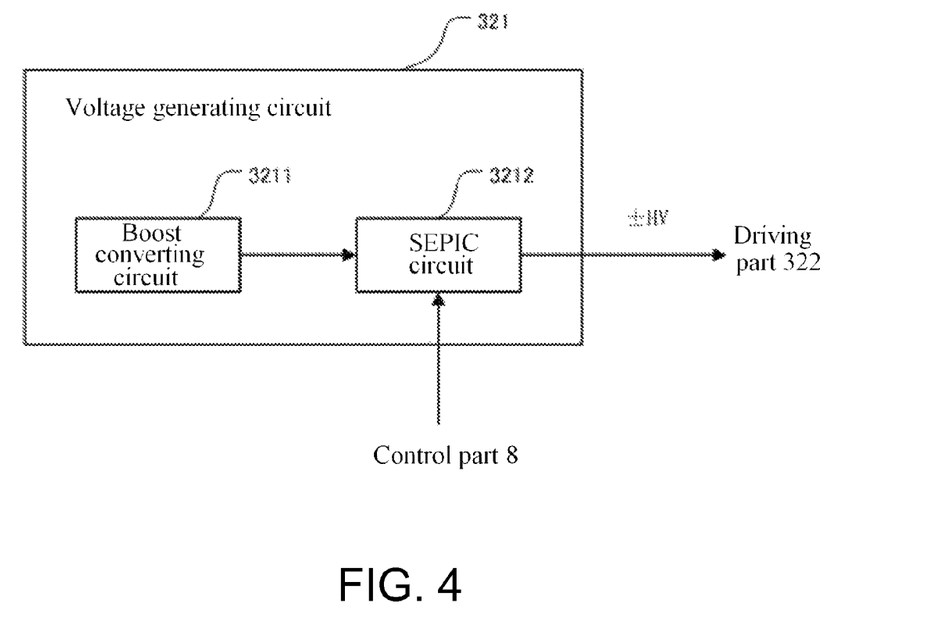
FIG. 4 is a block diagram showing a structure of a voltage generating circuit in the sending part as shown in FIG. 3.
Figure 5:
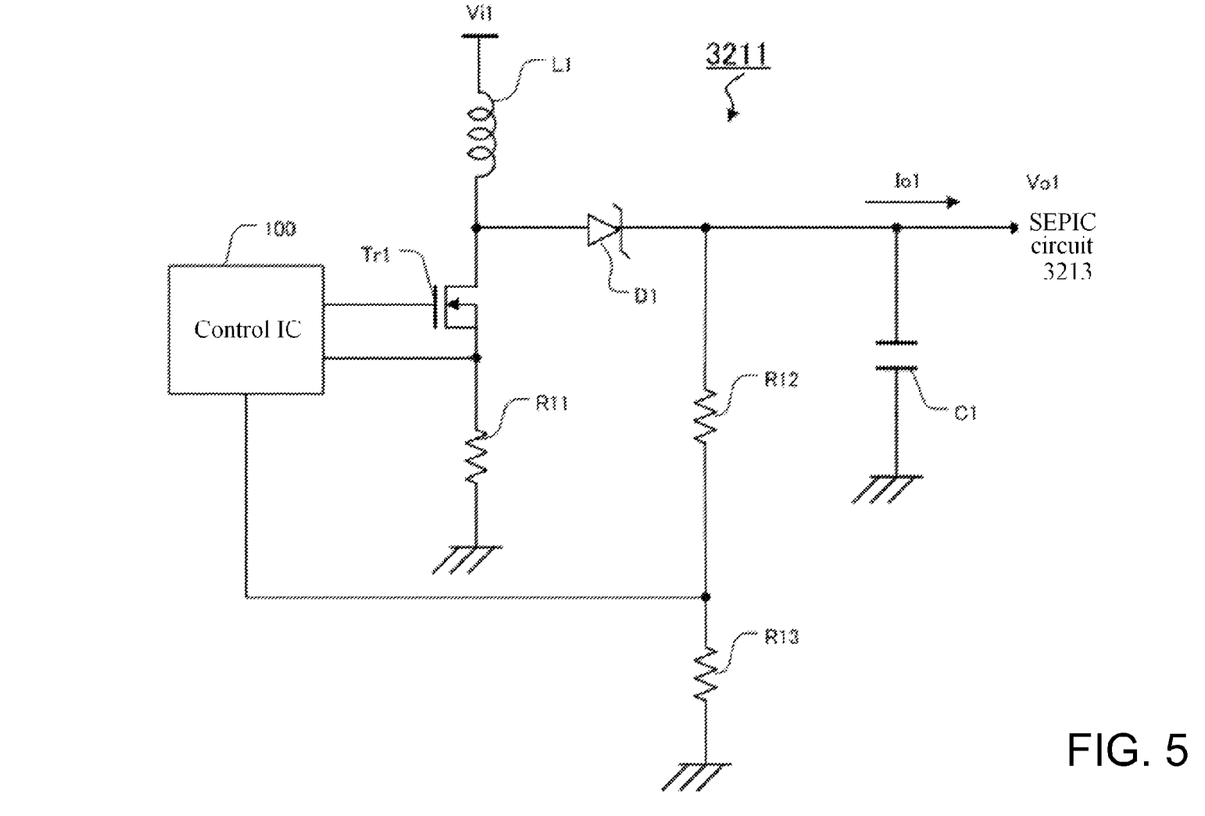
FIG. 5 is a diagram showing a circuit structure of a boost converting circuit in the voltage generating circuit as shown in FIG. 4.
Figure 6:
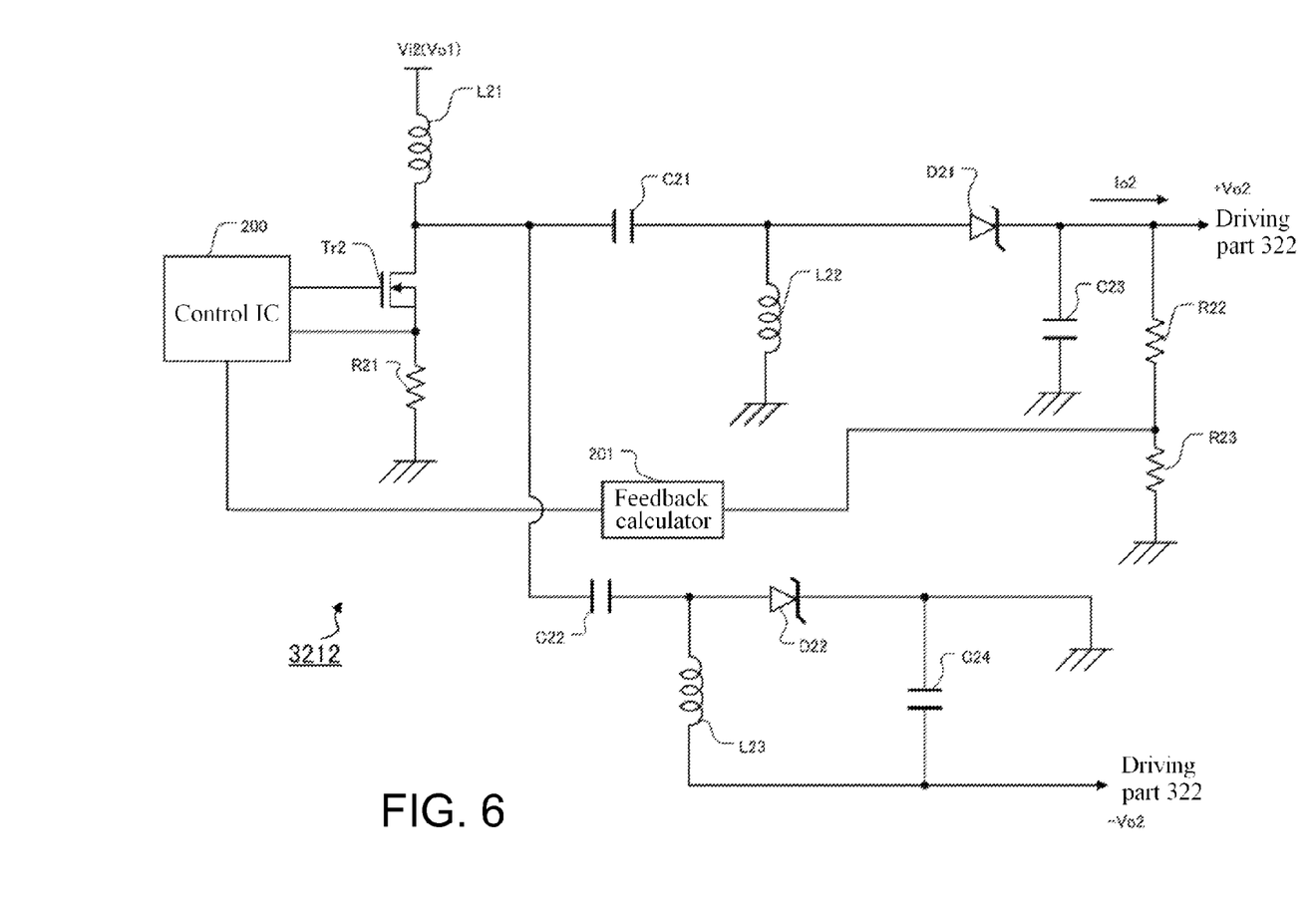
FIG. 6 is a diagram showing a circuit structure of an SEPIC circuit in the voltage generating circuit as shown in FIG. 4.

Embodiments of the invention will be described in detail below with reference to the accompanying drawings. FIG. 1 is a block diagram showing an example of an overall structure of an ultrasonic diagnosing device having the voltage generating circuit of the present invention. FIG. 2 is a block diagram showing a structure of an image acquiring part of the ultrasonic diagnosing device as shown in FIG. 1. FIG. 3 is a block diagram showing a structure of a sending part in the image acquiring part as shown in FIG. 2. FIG. 4 is a block diagram showing a structure of a voltage generating circuit in the sending part as shown in FIG. 3. FIG. 5 is a diagram showing a circuit structure of a boost converting circuit in the voltage generating circuit as shown in FIG. 4. FIG. 6 is a diagram showing a circuit structure of an SEPIC circuit in the voltage generating circuit as shown in FIG. 4.

An ultrasonic diagnosing device 1 as shown in FIG. 1 comprises an ultrasonic probe 2, an image acquiring part 3, an image storage part 4, an image display control part 5, a display part 6, an input part 7 and a control part 8.

The ultrasonic probe 2 has an array of ultrasonic oscillators (not shown) to transmit and receive an ultrasonic wave. The ultrasonic probe 2 that is in close contact with a surface of an examined body P irradiates an imaging cross section with an ultrasonic wave, and a sound ray as a time sequence receives an ultrasonic echo reflected from the inside of the examined body P. In addition, the ultrasonic probe 2 switches ultrasonic irradiation directions in turn and performs an electronic scan.

The image acquiring part 3 generates an electrical signal for driving the ultrasonic oscillators, and at the same time the electrical signal received by said ultrasonic oscillators is processed in B-mode or Doppler mode to form B-mode image information or Doppler image information. The image acquiring part 3 will be described later in detail.

The image storage part 4 consists of mass memories, which stores two-dimensional tomographic image information or cine image information of the two-dimensional tomographic image information that varies with time.

The image display control part 5 controls switching of display frame rates of the B-mode image information generated by the B-mode processing and the blood flow image information generated by the Doppler processing as well as shapes or positions displayed by the image.

The display part 6 consists of a Liquid Crystal Display (LCD), etc., which displays a B-mode image or a blood flow image, etc.

The input part 7 consists of a keyboard, etc., and an operator enters operation information through said input part 7. The information entered through said input part 7 can be, for example, operation information for selecting display of the B-mode processing or display of the Doppler mode processing, and operation information for setting a Doppler photographing area where the Doppler processing is performed, etc.

The control part 8 controls actions of the different parts of the ultrasonic diagnosing device 1 comprising the ultrasonic probe 2 based on the operation information entered through the input part 7 and pre-stored program or data.

The image acquiring part 3 is described in detail below with reference to FIG. 2. The image acquiring part 3 comprises a sending beamformer 31, a sending part 32, a receiving part 33, a receiving beamformer 34, a B-mode processing part 35 and a Doppler processing part 36.

The sending beamformer 31 generates an electrical signal having a specified delay time based on information from the control part 8, so that the ultrasonic probe 2 can perform electronic focusing of a focus depth position.

The sending part 32 forms a pulse train waveform for driving the ultrasonic oscillators of the ultrasonic probe 2 based on the electrical signal from the sending beamformer 31. Said sending part 32 will be described in detail later.

The receiving part 33 amplifies an initial section of the electrical signal received by the ultrasonic oscillators. The receiving beamformer 34 performs a delay computation on the electrical signal received by the receiving part 33 to form an electrical signal on the sound ray, where a specified delay time that is the same as the one in sending is applied to the computation.

The B-mode processing part 35 performs processing such as logarithmic transformation, filtering, etc. on the electrical signal on the sound ray obtained from the delay computation, thereby forming the B-mode image information. In addition, the Doppler processing part 36 performs vertical detection, filtering, etc. on the electrical signal on the sound ray obtained from the delay computation, thereby representing the blood flow information in the examined body P as frequency spectrum information or Color Flow Mapping (CFM) information.

The sending part 32 is described in detail with reference to FIG. 3. Said sending part 32 includes a voltage generating circuit 321 and a driving part 322. The voltage generating circuit 321 generates a positive and a negative voltages ±HV to be supplied to the driving part 322 as voltages for driving the ultrasonic oscillators of the ultrasonic probe 2. Moreover, the driving part 322 generates a driving signal for driving the pulse train waveform of the ultrasonic oscillators based on the electrical signal from the sending beamformer 3 1. Besides, the ±HV supplied from the voltage generating circuit 321 to the driving part 322 become voltages equivalent to an amplitude of the driving signal for driving the pulse train waveform of the ultrasonic oscillators.

The voltage generating circuit 321 is described in detail with reference to FIG. 4. The voltage generating circuit 321 is a power supply circuit that does not use any transformer, wherein a boost converting circuit 3211 and an SEPIC circuit 3212 are connected as two stages, that is, it is a structure of a series connection. In this embodiment, the first stage is the boost converting circuit 3211, and the second stage is the SEPIC circuit 3212. The first stage, i.e. the boost converting circuit 3211, is a constant voltage circuit with an output voltage Vo1 of the first stage being higher than an input voltage Vi1. Furthermore, the second stage, i.e. the SEPIC circuit 3212, is a circuit that makes an output voltage Vo2 of the second stage be a desired voltage. Details are described below.

The boost converting circuit 3211 uses a boost type of a power supply circuit, and the SEPIC circuit 3212 also uses a boost type of a power supply circuit. Moreover, the maximum of the output voltage Vo2 of the SEPIC circuit 3212 which is the second stage can be 20 times the input voltage Vi1 of the boost converting circuit 3211 which is the first stage. Specifically, the input voltage Vi1 is below 15V, and the output voltage Vo2 of ±10V~±70V can be obtained from said input voltage Vi1. As the output Vo2 of the SEPIC circuit 3212, the positive and negative voltages ±Vo2 with equal absolute values can be obtained.

Here in this embodiment, a battery (not shown) is used as a power supply of the voltage generating circuit 321. A voltage of the battery is supplied as the input voltage Vi1 to the boost converting circuit 3211. In this embodiment, the input voltage Vi is below 10V.

Suppose that only the SEPIC circuit is used as the voltage generating circuit 321, then in said SEPIC circuit, the maximum output voltage is 5 times the input voltage. If the output voltage falls, the color of the obtained ultrasonic image becomes lighter. Therefore, in order to ensure enough darkness, an output voltage of above 50V is sometimes necessary. If the battery is, for example, a lithium ion battery, an output voltage of above 10V would require a parallel connection of more than three lithium ion batteries. However, in this embodiment, through a two-stage power supply circuit, specifically through connecting the boost converting circuit 3211 and the SEPIC circuit 3212, the maximum output voltage Vo2 can be 20 times the input voltage. Thus the number of batteries connected in series can be reduced and miniaturization of the device is realized.

Structures of the boost converting circuit 3211 and the SEPIC circuit 3212 are described in detail below. First, the boost converting circuit 3211 is described with reference to FIG. 5. As shown in FIG. 5, the boost converting circuit 3211 comprises an inductor L1, a diode D1, resistors R11, R12, R13, and a capacitor C1. In addition, the boost converting circuit 3211 comprises a transistor Tr1 and a control IC 100. The transistor Tr1 is formed of an N-channel Metal Oxide Semiconductor Field Effect Transistor (MOS-FET), with a gate terminal connected to the control IC 100, a drain terminal connected to the inductor L1, and a source terminal grounded via the resistor R11. The transistor Tr1 is switched between on and off repeatedly through the control IC 100 so as to keep the output voltage Vo1 constant.

The control IC 100 is connected between the source terminal of the transistor Tr1 and the resistor R11 to control the switching of the transistor Tr1 through detecting a voltage across the resistor R11, thereby ensuring that an output current Io1 will not become an overcurrent.

Next, the SEPIC circuit 3212 is described with reference to FIG. 6. As shown in FIG. 6, the SEPIC circuit comprises inductors L21, L22, L23, diodes D21, D22, resistors R21, R22, R23, and capacitors C21, C22, C23, C24. In addition, the SEPIC circuit 3212 comprises a transistor Tr2, a control IC 200 and a feedback calculator 201. Besides, the SEPIC circuit 3212 is a circuit that can obtain the positive and negative voltages ±Vo2 as output voltages and the positive and negative electric power ±W2 as output electric power.

The transistor Tr2 is formed of an N-channel MOS-FET as the transistor Tr1. Further, a gate terminal of the transistor Tr2 is connected to the control IC 200. A drain terminal thereof is connected to the inductor L21. A source terminal is grounded via the resistor R21. The feedback calculator 201 is a feedback circuit for transforming the output voltages ±Vo2 into the desired voltages. The transistor Tr2 is switched between on and off repeatedly through the control IC 200 that receives a signal from the feedback calculator 201 so as to make the output voltages ±Vo2 become the desired voltages. The control IC 200, the feedback calculator 201 and the transistor Tr2 are one of the embodiments of an output voltage regulating part of the present invention.

The control IC 200 is connected between the source terminal of the transistor Tr2 and the resistor R21 to control the switching of the transistor Tr1 through detecting a voltage across the resistor R21, thereby ensuring that an output current Io2 will not become an overcurrent.

In an inverse converter as a conventional voltage generating circuit, a height of a transformer is at least 15 mm. By contrast, in the boost converting circuit 3211 and the SEPIC circuit 3212 in this embodiment, a height of the inductor is only 5 mm. Therefore, the voltage generating circuit 321 in this embodiment is much thinner than the conventional inverse converter.

In the voltage generating circuit 321 consisting of the boosting converting circuit 3211 and the SEPIC circuit 3212, the desired output voltage is generated that corresponds to a type of a transmission mode like B-mode or Doppler mode. That is, the output voltage Vo2 from the SEPIC circuit 3212 is variable, so it is a voltage set according to a transmission mode. Functions of the boost converting circuit 3211 and the SEPIC circuit 3212 are described in detail below.

First, the input voltage Vi1 is supplied from a power supply that is not shown in the figure to the boost converting circuit 3211 which is the first stage. Specifically, the input voltage Vi1 is below 15V. In the boost converting circuit 3211, the control IC 100 controls the switching of the transistor Tr1 to obtain the certain output voltage Vo1 (Vo1>Vi1).

The output voltage Vo1 of the boost converting circuit 3211 is supplied as the input voltage Vi2 to the SEPIC circuit 3212 which is the second stage. In the SEPIC circuit 3212, the control IC 200 controls the switching of the transistor Tr2 to obtain the desired output voltage Vo2 (Vo2>Vi2). The positive and negative voltages ±Vo2 can be obtained as the output voltage Vo2, and said output voltages ±Vo2 are supplied to the driving part 322 as the voltages ±HV for driving the ultrasonic oscillators of the ultrasonic probe 2.

According to the embodiment illustrated above, the two stages of the voltage generating circuit 321 have the boost converting circuit 3211 and the SEPIC circuit 3212 connected, so with respect to a low voltage below the input voltage of 15V, a maximum high output voltage that is 20 times the low input voltage can be obtained. Therefore, as with the conventional inverse converter, the voltage generating circuit generates a high output voltage from a relatively low input voltage. Further, the boost converting circuit 3211 and the SEPIC circuit 3212 are circuits that do not use any transformer, so they can be much thinner than the conventional inverse converter. In addition, since no transformer is used, the switching frequency can be increased and the volume of the circuit components can be reduced. By means of the above-described construction, the miniaturization and thinning of the mounting substrate can be realized.

Furthermore, according to this embodiment, an output voltage can be varied according to the types of the transmission mode like B-mode or Doppler mode.

Figure 7:
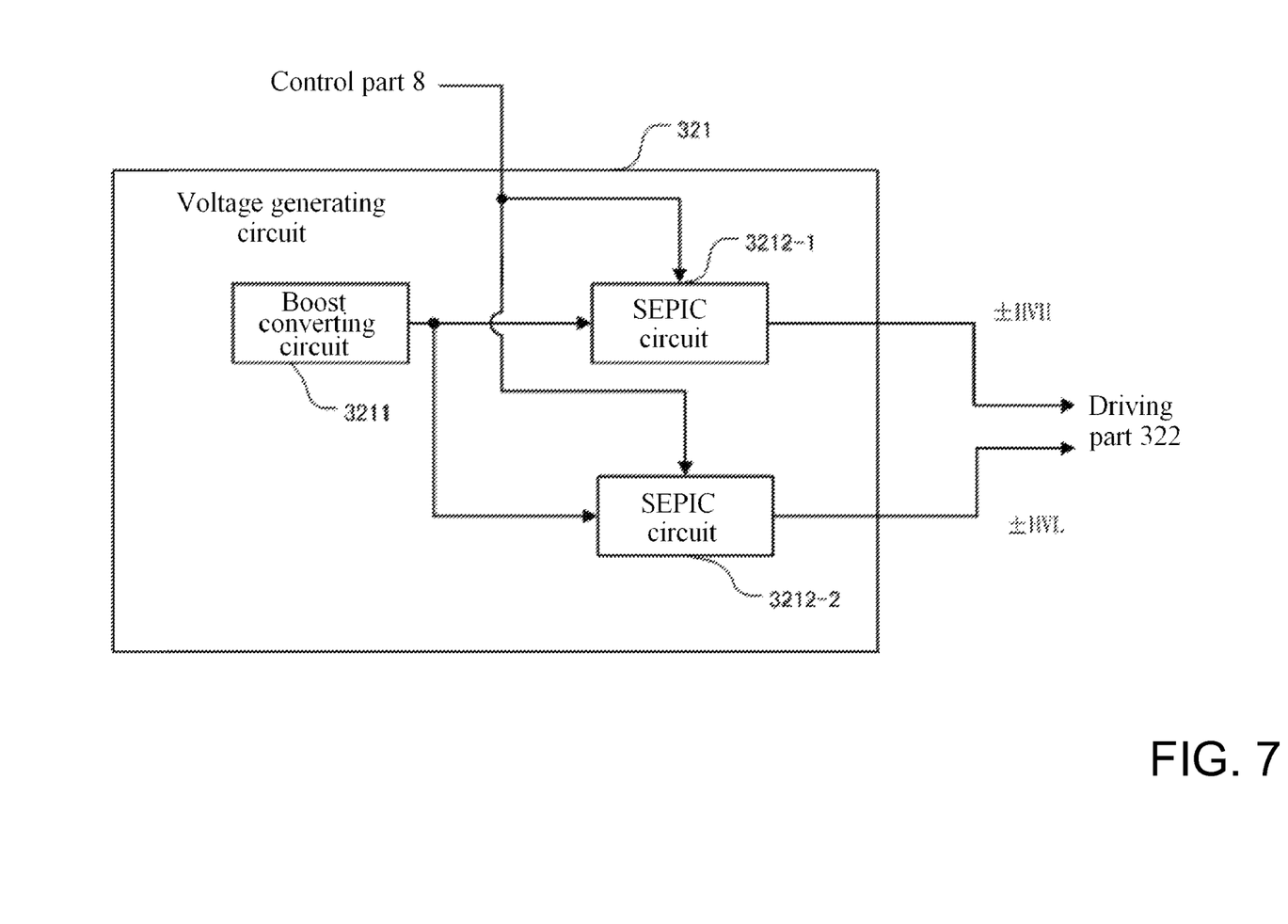
FIG. 7 is a diagram showing a first variation example of the embodiment of the voltage generating circuit of the present invention.

Next, a variation example of the above embodiment is described. First, the first variation example is described. FIG. 7 is a diagram showing a first variation example of the embodiment of the voltage generating circuit of the present invention, wherein the second stage of the power supply circuit has two SEPIC circuits 3212-1 and 3212-2. In each of the SEPIC circuits 3212-1 and 3212-2, the positive and negative output voltages with different absolute values can be ±HVH and ±HVL.

Figure 8:
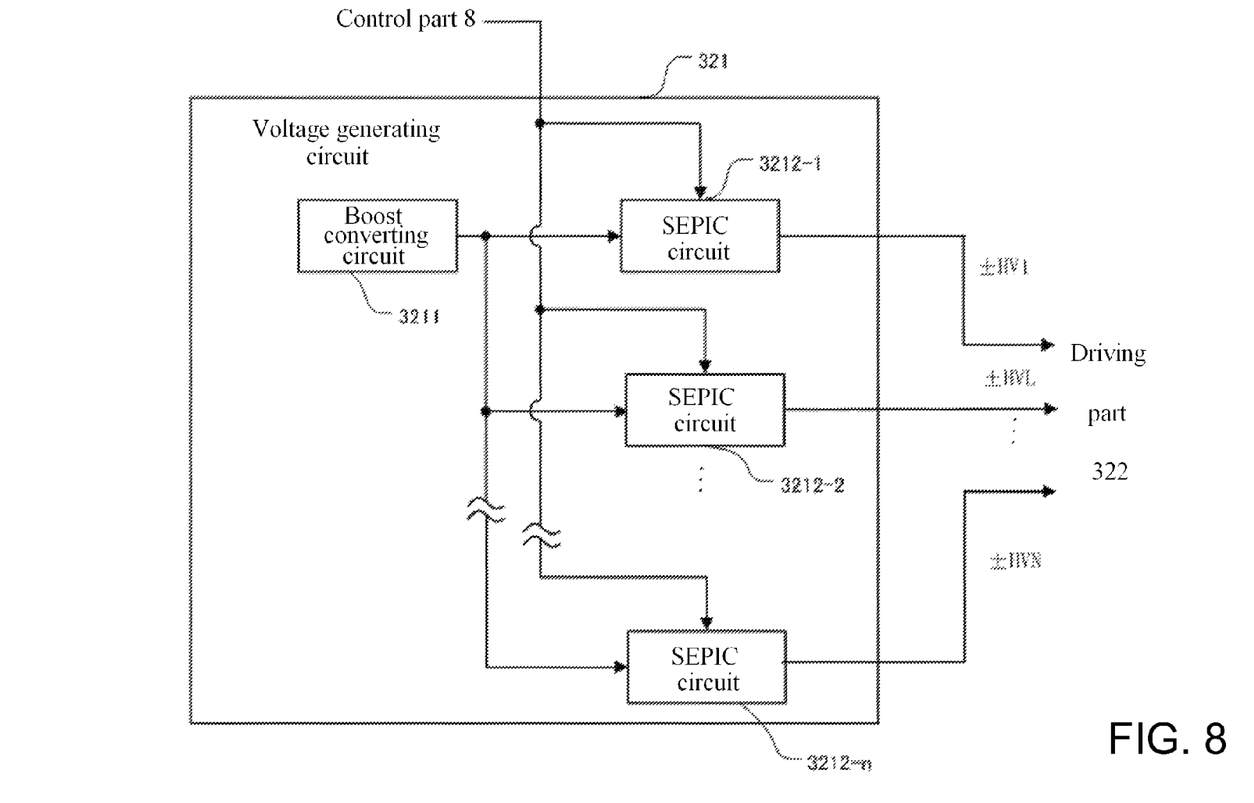
FIG. 8 is a diagram showing the voltage generating circuit of other examples of the first variation example as shown in FIG. 7.

In this first variation example, the number of the circuits in the second stage of the power supply circuit is not limited to two. That is, as shown in FIG. 8, the second stage of the power supply circuit can be n (n is a natural number greater than 1) SEPIC circuits 3212-1, 3212-2, . . . , 3212-n connected in parallel on the basis of the boost converting circuit 3211. At this time, preferably, the output voltages of the SEPIC circuits are output voltages ±HV1, ±HV2, . . . , ±HVN having different absolution values.

According to the first variation example, where a plurality of output voltages having different absolute values are obtained in the SEPIC circuits used as the second stage of the voltage generating circuit 321, the boost converting voltage 3211 used as the first stage can be shared so as to control the size of the mounting substrate.

Figure 9:
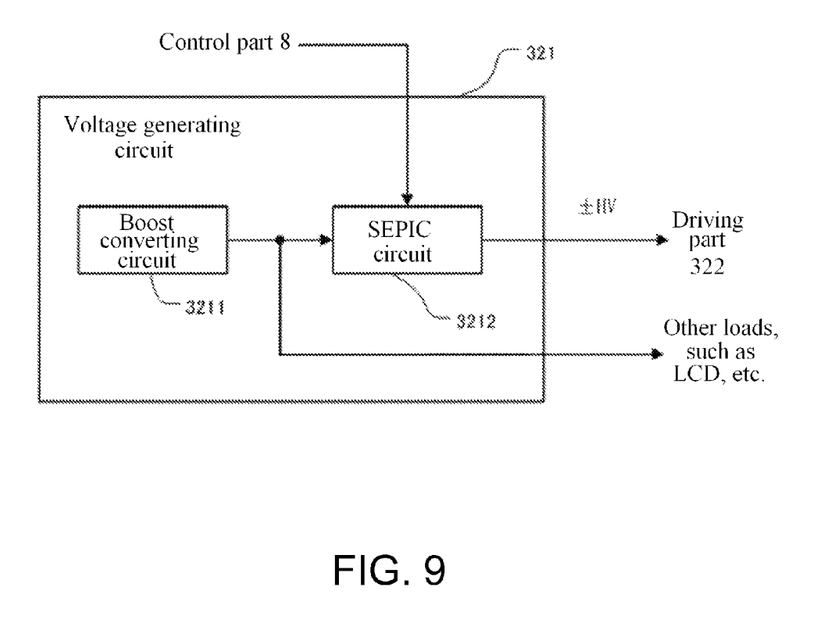
FIG. 9 is a diagram showing a second variation example of the voltage generating circuit of the present invention.

Next, a second variation example is described. FIG. 9 is a diagram showing the second variation example of the voltage generating circuit of the present invention. In the second variation example shown in FIG. 9, the output voltage of the boost converting circuit 3211 used as the first stage is supplied to the SEPIC circuit used as the second stage, and at the same time it can also be supplied to other loads, such as LCD, etc. that compose the display part 6, than the ultrasonic oscillators in the ultrasonic diagnosing device 1. Thus the boost converting circuit 3211 used as the first stage can be used as a power supply circuit that generates a voltage to be supplied to other loads than the ultrasonic oscillators in the ultrasonic diagnosing device 1, and control the size of the mounting substrate.

Figure 10:
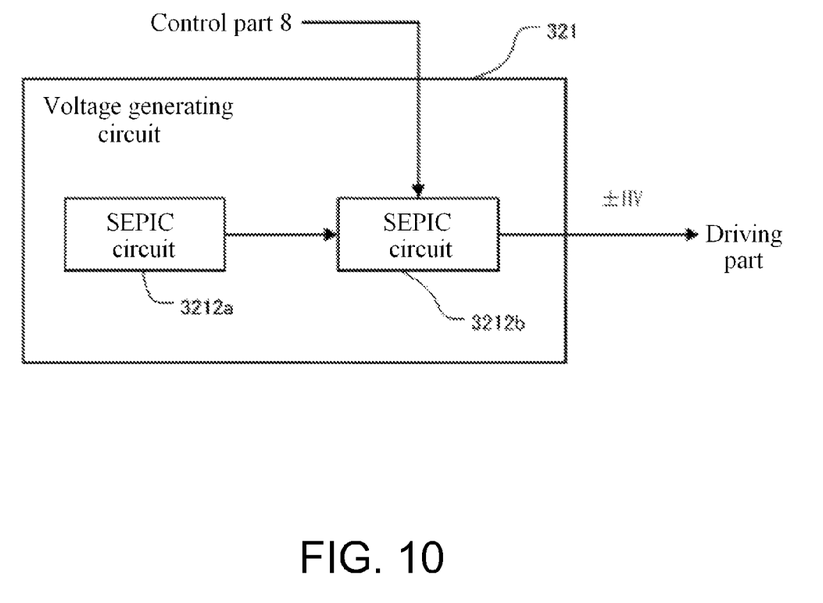
FIG. 10 is a diagram showing other examples of the embodiment of the voltage generating circuit of the present invention.

While the present invention is described above through the above embodiments, various modifications can be made to the invention without departing from its principle. For example, the power supply circuit forming the voltage generating circuit 321 can be a circuit whose first stage and second stage are both SEPIC circuits 3212a and 3212b, as shown in FIG. 10. However, in this case, output line of the SEPIC circuit 3212a used as the first stage can be only one, although no figure shows this.

In addition, in the case that the voltage generating circuit 321 is used in an ultrasonic diagnosing device that needs no negative voltage, although no figure shows this, as a power supply circuit forming said voltage generating circuit 321, the first stage of the power supply circuit can be an SEPIC circuit and the second stage of the power supply circuit can be a boost converting circuit. Further, the first stage of and the second stage of the power supply circuit forming said voltage generating circuit 321 are both boost converting circuits.

Further, in the above embodiment, the SEPIC circuit 3212 used as the second stage has the feedback calculator 201 with a variable output voltage, but a feedback calculator with a variable output voltage can also be formed in the first stage of the power supply circuit.

What is claimed is:
1. A voltage generating circuit configured to generate an output voltage for use in driving an ultrasonic oscillator, said voltage generating circuit comprising a multi-stage connected power supply circuit without a transformer that comprises a boost converting circuit connected in series with a single ended primary inductance converter (SEPIC) circuit.

2. The voltage generating circuit according to claim 1, wherein at least one stage of said multi-stage power supply circuit comprises an output voltage regulating part configured to regulate the output voltage such that the output voltage is a desired voltage.

3. The voltage generating circuit according to claim 2, wherein said multi-stage power supply circuit comprises a two-stage power supply circuit.

4. The voltage generating circuit according to claim 3, wherein said two-stage power supply circuit comprises a first stage comprising one of said boost converting circuit and said SPEIC circuit having a constant voltage circuit output voltage higher than a constant voltage circuit input voltage, and a second stage comprising said other of said boost converting circuit and said SPEIC circuit with said output voltage regulating part.

5. The voltage generating circuit according to claim 1, wherein a maximum of the output voltage obtained from said voltage generating circuit is 20 times an input voltage of the voltage generating circuit.

6. The voltage generating circuit according to claim 1, wherein an input voltage of the voltage generating circuit is less than 15 Volts (V) and an absolute value of the output voltage is between 10V and 70V.

7. The voltage generating circuit according to claim 1, further comprising a battery used to supply an input voltage to the multi-stage power supply circuit.

8. The voltage generating circuit according to claim 4, wherein said first stage comprises said boost converting circuit, and said second stage comprises said SEPIC circuit.

9. The voltage generating circuit according to claim 8, wherein said SEPIC circuit of said second stage is configured to generate a positive voltage and a negative voltage having equal absolute values as the output voltage.

10. The voltage generating circuit according to claim 4, wherein said first stage comprises said SEPIC circuit, and said second stage comprises said boost converting circuit.

11. The voltage generating circuit according to claim 4, wherein said second stage comprises a plurality of circuits.

12. The voltage generating circuit according to claim 11, wherein said plurality of circuits of said second stage are each configured to generate respective output voltages having different absolute values from one another.

13. The voltage generating circuit according to claim 4, wherein a voltage generated by said first stage is supplied to said second stage and to other loads than said ultrasonic oscillator in an ultrasonic diagnosing device.

14. The voltage generating circuit according to claim 2, wherein said voltage regulating part is configured to regulate the output voltage according to a type of a transmission mode of an ultrasonic wave.

15. An ultrasonic diagnosing device comprising:
an ultrasonic oscillator; and
a voltage generating circuit coupled to said ultrasonic oscillator, said voltage generating circuit comprising a multi-stage connected power supply circuit without a transformer that comprises a boost converting circuit connected in series with a single ended primary inductance converter (SEPIC) circuit.

16. The ultrasonic diagnosing device according to claim 15, wherein at least one stage of said multi-stage power supply circuit comprises an output voltage regulating part configured to regulate an output voltage of the multi-stage power supply circuit such that the output voltage is a desired voltage.

17. The ultrasonic diagnosing device according to claim 16, wherein said multi-stage power supply circuit comprises a two-stage power supply circuit.

18. The ultrasonic diagnosing device according to claim 17, wherein said two-stage power supply circuit comprises a first stage comprising one of said boost converting circuit and said SPEIC circuit having a constant voltage circuit output voltage higher than a constant voltage circuit input voltage, and a second stage comprising said other of said boost converting circuit and said SPEIC circuit with said output voltage regulating part.

* * * * *

UNITED STATES PATENT AND TRADEMARK OFFICE
CERTIFICATE OF CORRECTION

PATENT NO. : 8,138,823 B2  
APPLICATION NO. : 12/509203  
DATED : March 20, 2012  
INVENTOR(S) : Zang et al.

Page 1 of 1

It is certified that error appears in the above-identified patent and that said Letters Patent is hereby corrected as shown below:

In Column 1, Lines 10-16, delete "CROSS REFERENCE..........in its entirety." and insert the same at line 3, before "FIELD OF THE INVENTION".

In Column 5, Line 56, delete "3 1." and insert -- 31. --, therefor.

In Column 9, Line 12, in Claim 4, delete "SPEIC" and insert -- SEPIC --, therefor.

In Column 9, Line 15, in Claim 4, delete "SPEIC" and insert -- SEPIC --, therefor.

In Column 10, Line 32, in Claim 18, delete "SPEIC" and insert -- SEPIC --, therefor.

In Column 10, Line 35, in Claim 18, delete "SPEIC" and insert -- SEPIC --, therefor.

Signed and Sealed this  
Twenty-sixth Day of June, 2012

David J. Kappos  
*Director of the United States Patent and Trademark Office*